United States Patent [19]

Isenring et al.

[11] Patent Number: 5,036,074
[45] Date of Patent: Jul. 30, 1991

[54] CERTAIN 2,4-DICHLORO-PHENYL(LOWERALKYLIDENE) PYRIDINES HAVING FUNGICIDAL ACTIVITY

[75] Inventors: Hans P. Isenring, Sissach; Beat Zehnder, Reinach; Hugo Ziegler, Allschwil, all of Switzerland

[73] Assignee: Ciba-Geigy Corporation, Ardsley, N.Y.

[21] Appl. No.: 481,264

[22] Filed: Feb. 20, 1990

[30] Foreign Application Priority Data

Mar. 1, 1989 [CH] Switzerland ............................ 747/89

[51] Int. Cl.$^5$ ...................... C07F 5/00; C07D 213/26; C07D 213/61; A01N 43/40
[52] U.S. Cl. ........................................ 514/277; 546/5; 546/339; 546/346
[58] Field of Search ........................... 546/346, 5, 339; 514/277

[56] References Cited

PUBLICATIONS

Fieser and Fieser "Reagents for Organic Synthesis", vol. 6, p. 647, Wiley–Interscience publishers QD 262 FS (1977).

Primary Examiner—Alan L. Rotman
Attorney, Agent, or Firm—Edward McC. Roberts

[57] ABSTRACT

The invention concerns new pyridine derivatives of the formula

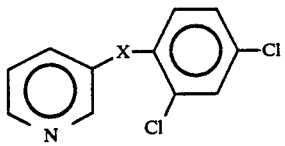

I wherein X signifies a group

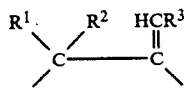

(a)

or

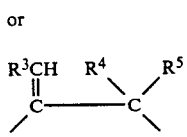

(b)

and $R^1$, $R^2$, $R^3$, $R^4$ and $R^5$ have the significances given in the description, and their N-oxides, N-amino salts, copper complexes and acid addition salts, processes for the manufacture of these substances, fungicidal compositions which contain these substances as the active ingredient and the use of such substances and compositions for the control of fungi in agriculture and in horticulture.

10 Claims, No Drawings

CERTAIN 2,4-DICHLORO-PHENYL(LOWERALKYLIDENE) PYRIDINES HAVING FUNGICIDAL ACTIVITY

SUMMARY OF THE INVENTION

The invention concerns new pyridine derivatives of the formula

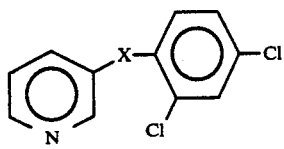

I wherein X signifies a group

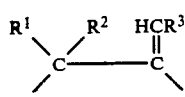

(a)

or

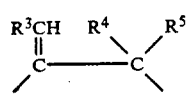

(b)

and $R^1$, $R^2$, $R^3$, $R^4$ and $R^5$ have the significances given in the description, and their N-oxides, N-amino salts, copper complexes and acid addition salts, processes for the manufacture of these substances, fungicidal compositions which contain these substances as the active ingredient and the use of such substances and compositions for the control of fungi in agriculture and in horticulture.

DETAILED DESCRIPTION OF THE INVENTION

The present invention is concerned with heterocyclic compounds, namely pyridine derivatives of the formula

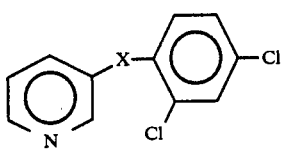

I wherein
X signifies a group (a) or (b)

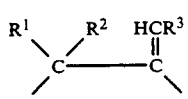

(a)

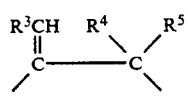

(b)

$R^1$ and $R^2$ signify methyl or together form ethylene,
$R^3$ signifies hydrogen, chlorine, $C_{1-4}$-alkyl or methoxy, $R^4$ signifies hydrogen or methyl and
$R^5$ signifies methyl or, where $R^4$ signifies hydrogen, also $C_{1-4}$-alkyl, allyl or propargyl or
$R^4$ and $R^5$ together form ethylene, as well as the N-oxides, N-amino salts and copper complexes of the compounds of formula I and finally the acid addition salts of the compounds of formula I and of their N-oxides.

The invention is also concerned with a process for the manufacture of the compounds in accordance with the invention, fungicidal compositions which contain such compounds as the active ingredient as well as the use of such compounds and compositions for the control of fungi in agriculture and in horticulture.

Under the term "N-amino salts" there are to be understood the compounds of formula I in which the 3-pyridyl group is modified in accordance with the following formula:

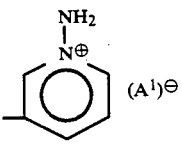

wherein $(A^1)^\ominus$ signifies the anion of a physiologically compatible acid.

Examples of such acids are alkanecarboxylic acids, benzoic acid and it nuclear-substituted derivatives such as, for example, alkyl-, nitro- and/or chloro-substituted benzoic acids, optionally substituted benzenesulphonic acid; carbamic acid, hydrochloric acid, hydrobromic acid, hydroiodic acid and sulphuric acid.

As the acid addition salts of the compounds of formula I there come into consideration physiologically compatible salts. Hereto there preferably belong salts of these compounds with inorganic and organic acids such as hydrochloric acid; nitric acid; phosphoric acid; mono- and bifunctional carboxylic acids and hydroxycarboxylic acids, e.g. acetic acid, maleic acid, succinic acid, fumaric acid, tartaric acid, citric acid, salicylic acid, sorbic acid and lactic acid; and sulphonic acids, e.g. 1, 5-naphthalene-disulphonic acid.

The N-oxides of the compounds of formula I can also form salts with suitable acids. As such acid addition salts there come into consideration physiologically compatible salts, preferably salts with strong acids such as inorganic acids, e.g. hydrochloric acid, nitric acid and phosphoric acid, and sulphonic acids, e.g. 1, 5-naphthalene-disulphonic acid.

By the term "copper complexes" there are meant especially copper(II) complexes of the formula

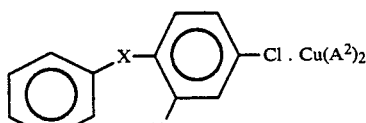

in which $A^2$ signifies the anion of an organic or inorganic acid such as formic acid, acetic acid, propionic acid, benzoic acid, oxalic acid, tartaric acid, lactic acid, salicylic acid, citric acid, carbonic acid, sulphuric acid, nitric acid or hydrochloric acid. $A^2$ preferably signifies acetate.

The compounds can be present as E- and Z-isomers and/or as atropic isomers. Formula I is intended to embrace all of these possible isomeric forms and their mixtures.

Preferably, $R^1$ and $R^2$ in formula I together signify ethylene. Independently of the significances of $R^1$ and $R^2$ and independently of one another, $R^3$ preferably signifies hydrogen or methoxy, $R^4$ preferably signifies hydrogen and $R^5$ preferably signifies methyl.

Especially preferred individual compounds in accordance with the invention are:

3-(2,4-Dichloro-α,α-dimethyl-β-methylenephenethyl)-pyridine,

3-[1-(2,4-dichloro-α-methylenebenzyl)-cyclopropyl]-pyridine, the 1:1 complex of 3-[1-(2,4-dichloro-α-methylenebenzyl)-cyclopropyl]-pyridine and copper(II) acetate, 3-[1-(2,4-dichloro-α-methylenebenzyl)-cyclopropyl]-pyridine 1-oxide, 3-[1-(2,4-dichloro-α-methoxymethylenebenzyl)-cyclopropyl]-pyridine, 3-[1-(2,4-dichloro-α-ethylidenebenzyl)-cyclopropyl]-pyridine, 3-(2,4-dichloro-α-methoxymethylene-β-methylphenethyl)-pyridine, 3-(α-butylidene-2,4-dichloro-8-methylphenethyl)-pyridine, 3-(2,4-dichloro-β,β-dimethyl-α-methylenephenethyl)-pyridine, 3-[2,4-dichloro-α-methylene-8-(2-propynyl)-phenethyl]-pyridine, 3-[2,4-dichloro-α-methoxymethylene-β-(2-propynyl)-phenethyl]-pyridine, 3-(2,4-dichloro-α-methylene-8-propylphenethyl)-pyridine, 3-(α-chloromethylene-2,4-dichloro-β-methylphenethyl)-pyridine, 3-[α-chloromethylene-2,4-dichloro-β-(2-propynyl)-phenethyl]-pyridine, 3-(β-allyl-2,4-dichloro-α-methylenephenethyl)-pyridine, the 1:1 complex of 3-(α-butylidene-2,4-dichloro-β-methylphenethyl)-pyridine and copper(II) acetate, 3-[α-butylidene-2,4-dichloro-β-(2-propynyl)-phenethyl]-pyridine, 3-(2,4-dichloro-β-methyl-α-methylenephenethyl)-pyridine, the 1:1 complex of 3-(2,4-dichloro-β-methyl-α-methylenephenethyl)-pyridine and copper(II) acetate and 3 (2,4-dichloro-β-ethyl-α-methoxymethylenephenethyl)-pyridine, especially the second-mentioned compound of the above list.

Further representatives of the compounds in accordance with the invention are:

3-(2,4-Dichloro-α-ethylidene-β-methylphenethyl)-pyridine, the 1:1 complex of 3-(2,4-dichloro-B, B-dimethyl-a-methylenephenethyl)-pyridine and copper(II) acetate, the 1:1 complex of 3-(α-butylidene-2,4-dichloro-β-methylphenethyl)-pyridine and copper(II) acetate, 3-(2,4-dichloro-β-methyl-α-propylidenephenethyl)-pyridine, the 1:1 complex of 3-(2,4-dichloro-β-methyl-α-propylidenephenethyl)-pyridine and copper(II) acetate, the 1:1 complex of 3-[2,4-dichloro-α-methoxymethylene-β-(2-propynyl)-phenethyl]-pyridine and copper(II) acetate, 3-(2,4-dichloro-β-methyl-α-methylenephenethyl)-pyridine 1-oxide, 1-amino-3-(2,4-dichloro-β-methyl-α-methylenephenethyl)-pyridinium 2,4, 6-trimethylbenzenesulphonate and 1-amino-3-[1-(2,4-dichloro-α-methylenebenzyl)-cyclopropyl]-pyridinium 2,4, 6-trimethylbenzenesulphonate.

The process in accordance with the invention for the manufacture of the compounds in accordance with the invention comprises a) reacting a ketone of the formula

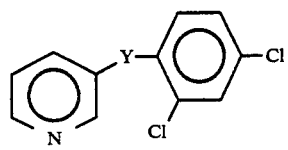

wherein Y signifies a group (a') or (b')

and $R^1$, $R^2$, $R^4$ and $R^5$ have the significances given above, with a triphenylphosphonium salt of the formula

wherein $R^3$ has the significance given above and Hal⊖ signifies a chloride or bromide ion, (b) for the manufacture of the N-oxide or of a N-amino salt of a compound of formula I, N-oxidizing this or reacting this with an amine derivative of the formula

wherein $A^3$ signifies the residue of a physiologically compatible acid, (c) for the manufacture of an acid addition salt of a compound of formula I or of its N-oxide, reacting the compound of formula I or its N-oxide with an acid, or (d) for the manufacture of a copper complex of a compound of formula I, reacting this with a copper salt of the formula

wherein $A^2$ has the significance given above.

Process variant a) is conveniently carried out by suspending a triphenylphosphonium salt of formula III in an inert diluent such as an aromatic hydrocarbon, e.g. benzene or toluene, an aliphatic or cyclic ether, e.g. 1, 2-dimethoxyethane, tetrahydrofuran or dioxan, or a dialkylamide, e.g. dimethylformamide, and reacting with a base such as an alkali metal hydride, e.g. sodium hydride, an alkali metal alcoholate, e.g. sodium methylate or potassium tert.butylate, an alkali metal amide, e.g. sodium amide, or a lithium alkyl, e.g. n-butyllithium, at temperatures between −20° C. and the reflux temperature of the reaction mixture, preferably in the temperature range of 0° C. to 80° C. Thereafter, a ketone of formula II, in undissolved form or conveniently dissolved in one of the above-mentioned diluents, is added and the reaction mixture is held in the temperature range of −75° C. up to the reflux temperature, preferably between +20° C. and 80° C. The mixture of a triphenylphosphonium salt with sodium amide, which is marketed as "Instant-Ylide" (Fluka), is especially suitable as the triphenylphosphonium salt and base.

The N-oxide formation according to process variant (b) is conveniently effected under those reaction conditions which are described in European Patent Specification No. 74018, page 5, lines 47–61, for the N-oxidation of pyridine and pyrazine derivatives.

The N-amination of a compound of formula I with an amine derivative of formula IV, i.e. process variant (b), is conveniently carried out by treating the compound I with the amine derivative in an inert organic diluent such as a halogenated aliphatic hydrocarbon, e.g. methylene chloride or chloroform, at temperatures between 0° C. and the reflux temperature of the reaction mixture.

For the manufacture of the acid addition salts, the compounds I or their N-oxides are reacted with the desired acids in the usual manner.

Process variant (d) is conveniently carried out by stirring together intensively a solution of the compound of formula I in an inert water-immiscible diluent such as a halogenated aliphatic hydrocarbon, e.g. methylene chloride or chloroform, and an aqueous solution of the copper salt of formula V.

The isolation and purification of the thus-manufactured compounds of formula I and their N-oxides, N-amino salts, acid addition salts and copper complexes can be effected according to methods known per se. Likewise, isomer mixtures, e.g. E/Z-isomer mixtures, which may be obtained can be separated into the pure isomers according to methods known per se, for example by chromatography or fractional crystallization.

The ketones of general formula II which are used as starting materials in process variant a) are either known or can be produced according to methods known per se [see e.g. European Patent Publications Nos. 74018 and 117485 as well as—in the case of the production of the cyclopropyl ketones of formula II ($R^1$ and $R^2$ or $R^4$ and $R^5$ together signify ethylene)—Tetrahedron Letters, 25, 5501 (1984)]. Likewise, the reagents of formulae III and IV are known and can be produced according to known methods.

The compounds in accordance with the invention possess fungicidal activity and can accordingly be used for the control of fungi in agriculture, in horticulture as well as in the processing of wood. They are especially suitable for inhibiting the growth of phytopathogenic fungi or for destroying phytopathogenic fungi on parts of plants, e.g. leaves, stems, roots, bulbs, tubers, fruits or flowers, and on seeds as well as in soil. Further, fungi which destroy and discolour wood can be controlled with the compounds in accordance with the invention. The compounds in accordance with the invention are especially effective in the control of fungi of the classes Deuteromycetes, Ascomycetes and Basidiomycetes such as, for example, Botrytis cinerea, Erysiphe cichoracearum, Erysiphe graminis, Uncinula necator, Podosphaera leucotricha, Venturia inaequalis, Cercospora archidicola, Cercospora beticola and Mycosphaerella fijiensis as well as of harmful fungi of the genera Sphaerotheca, Puccinia, Uromyces, Hemileia, Rhizoctonia, Alternaria, Cercosporella, Ceratocystis (e.g. Ceratocystis ulmi and Ceratocystis fimbriata), Verticillium, Fusarium, Helmithosporium, Sclerotinia, Penicillium, Septona, Ustilago, Tilletia, Coniophora, Cloeophyllum and Aureobasidium.

The compounds in accordance with the invention are distinguished by local and/or systemic activity.

The compounds in accordance with the invention are active against phytopathogenic fungi under greenhouse conditions even at concentrations of 1 mg to 500 mg of active ingredient per liter of spray liquor. In the open, concentrations of 25 g to 1500 g of active ingredient of formula I per hectare and treatment are advantageously used. For the control of seed-borne or soil-borne fungi in a dressing process there are advantageously used 0.05 g to 1.5 g of active ingredient of formula I per kg of seeds.

The above-mentioned starting materials of general formula II are also valuable as fungicides, since they have a similar spectrum of activity to the compounds of formula I. These starting materials can accordingly also be used for the control of fungi in agriculture and in horticulture, namely in the same manner as the compounds in accordance with the invention.

The compounds in accordance with the invention can be formulated to give a wide variety of compositions, e.g. solutions, suspensions, emulsions, emulsifiable concentrates and pulverous preparations. The fungicidal compositions in accordance with the invention contain an effective amount of at least one compound of general formula I, as defined above, or of a N-oxide, N-amino salt, acid addition salt or copper complex of such a compound as well as formulation adjuvants. The compositions conveniently contain at least one of the following formulation adjuvants:

Solid carrier substances; solvents or dispersion media; tensides (wetting and emulsifying agents); dispersing agents (without tenside action); and stabilizers.

As solid carrier substances there essentially come into consideration: natural mineral substances such as kaolin, aluminas, siliceous earth, talc, bentonite, chalk, e.g. whiting, magnesium carbonate, limestone, quartz, dolomite, attapulgite, montmorillonite and diatomaceous earth; synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as granulates or powders.

As solvents or dispersion media there essentially come into consideration: aromatics such as toluene, xylenes, benzene and alkylnaphthalenes, chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol as well as their ethers and esters; ketones such as acetone, methyl ethyl ketone, methyl isobutyl ketone and cyclohexanone; and strongly polar solvents or dispersion media such as dimethylformamide, N-methylpyrrolidone and dimethyl sulphoxide, such solvents or dispersion media preferably having flash points of at least 30° C. and boiling Points of at least 50° C, and water. Among the solvents or dispersion media there also come into consideration so-called liquified gaseous extenders or carrier substances, these being products which are gaseous at room temperature and under normal pressure. Examples of such products are especially aerosol propellants such as halogenated hydrocarbons, e.g. dichlorodifluoromethane. When water is used as the solvent, organic solvents can e.g. also be used as auxiliary solvents.

The tensides (wetting and emulsifying agents) can be non-ionic compounds such as condensation products or fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzenesulphonates, e.g. calcium dodecylbenzenesulphonate, and butylnaphthalene sulphonates; and more complex fatty sulphonates, e.g. the amide condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside activity) there essentially come into consideration: lignin, sodium and ammonium salts of lignin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides; antioxidants, e.g. gallic acid esters and butylhydroxytoluene; UV-absorbers, e.g. substituted benzophenones, diphenylacrylonitrile acid esters and cinnamic acid esters; and deactivators, e.g. salts of ethylenediaminetetraacetic acid and polyglycols.

The fungicidal compositions in accordance with the invention can contain, in addition to the active ingredients of formula I, other active ingredients, e.g. other fungicidal agents, insecticidal and acaricidal agents, bactericides, plant growth regulators and fertilizers. Such combination compositions are suitable for broadening the spectrum of activity or for specifically influencing the plant growth.

The fungicidal compositions in accordance with the invention generally contain, according to type, between 0.0001 and 95 weight percent of compound in accordance with the invention or compounds in accordance with the invention as the active ingredient(s). They can be present in a form which is suitable for storage and transport. In such forms, e.g. emulsifiable concentrates, the active ingredient concentration is normally in the higher region of the above concentration range. These forms can be diluted with the same or different formulation adjuvants to give active ingredient concentrations which are suitable for practical use and such concentrations normally lie in the lower region of the above concentration range. Emulsifiable concentrates generally contain 5 to 95 weight percent, preferably 25 to 75 weight percent, of the compound or compounds of formula I. As forms of use there come into consideration, inter alia, ready-for-use solutions, emulsions and suspensions which are suitable, for example, as spray liquors. In such spray liquors there can be present e.g. concentrations between 0.0001 and 20 weight percent. In the Ultra-Low-Volume process there can be formulated spray liquors in which the active ingredient concentration is preferably from 0.5 to 20 weight percent, while the spray liquors formulated in the Low-Volume process and in the High-Volume process preferably have an active ingredient concentration of 0.02 to 1.0 and 0.002 to 0.1 weight percent, respectively.

The fungicidal compositions in accordance with the invention can be manufactured by mixing at least one compound in accordance with the invention with formulation adjuvants.

The manufacture of the compositions can be carried out in a known manner, e.g. by mixing the active ingredient with solid carrier substances, by dissolution or suspension in suitable solvents or dispersion media, if necessary with the use of tensides as wetting or emulsifying agents or of dispersing agents, by diluting Pre-prepared emulsifiable concentrates with solvents or dispersion media etc.

In the case of pulverous compositions the active ingredient can be mixed with a solid carrier substance, e.g. by grinding them together; or the solid carrier substance can be impregnated with a solution or suspension of the active ingredient and then the solvent or dispersion medium can be removed by evaporation, heating or by sucking-off under reduced pressure. By adding tensides or dispersing agents such pulverous compositions can be made readily wettable with water, so that they can be converted into aqueous suspensions which are suitable e.g. as spray compositions.

The compounds in accordance with the invention can also be mixed with a tenside and a solid carrier substance to form a wettable powder which is dispersible in water or they can be mixed with a solid pre-granulated carrier substance to form a product in the form of a granulate.

When desired, a compound in accordance with the invention can be dissolved in a water-immiscible solvent such as, for example, an alicyclic ketone, which conveniently contains dissolved emulsifying agent, so that the solution becomes self-emulsifying upon addition to water. Alternatively, the active ingredient can be mixed with an emulsifying agent and the mixture can then be diluted with water to the desired concentration. Moreover, the active ingredient can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the compositions in accordance with the invention can be carried out according to the application methods which are usual in plant protection or in agriculture. The method in accordance with the invention for the control of fungi comprises treating the locus to be protected, e.g. plants, parts of plants or seeds, with an effective amount of a compound in accordance with the invention or of a composition in accordance with the invention.

The following Examples illustrate the invention.

Manufacture of the active substances of formula I

EXAMPLE 1

135 ml of n-butyllithium (1.6M in n-hexane) are added dropwise at 0° C. under argon to a suspension of 73.9 g (0.215 mol) of methoxymethyltriphenylphosphonium chloride in 500 ml of anhydrous tetrahydrofuran in such a manner that the temperature does not exceed 5° C. After stirring at 0° C. for 30 minutes a solution of 50 g (0.178 mol) of 2-(2,4-dichlorophenyl)-1-(3-pyridyl)-1-propanone in 100 ml of dry tetrahydrofuran is added dropwise at −75° C. within 30 minutes. The mixture is stirred at this temperature for 3 hours and 100 ml of water are then added dropwise at 0° C. The tetrahydrofuran is distilled off under reduced pressure and the residue is extracted with ethyl acetate. After distilling off the ethyl acetate the oily residue is chromatographed on silica gel with dichloromethane/ethyl acetate (95:5 vol%) as the eluent. There is thus obtained with the 1st fraction (E)-3-(2,4-dichloro-α-methoxymethylene-β-methylphenethyl)-pyridine as beige crystals, m.p. 67–68° C., and with the 2nd fraction (Z)-3-(2,4-dichloro-α-methoxymethylene-β-methylphenethyl)-pyri dine as a yellowish oil in the ratio of about 1:1 in a total amount of 44.4 g.

In an analogous manner, starting from 2-(2,4-dichlorophenyl)-1-(3-pyridyl)-1-propanone and butyltriphenylphosphonium bromide there is obtained 3-(α-butylidene-2,4-dichloro-β-methyl-phenethyl)-pyridine.
  1st isomer: yellow oil,
  2nd isomer: yellow oil;

starting from 2-(2,4-dichlorophenyl)-1-(3-pyridyl)-1-propanone and ethyltriphenylphosphonium bromide there is obtained 3-(2, 4-dichloro-α-ethylidene-β-methylphenethyl)-pyridine as a colourless oil;

starting from 2-(2,4-dichlorophenyl)-1-(3-pyridyl)-1-propanone and chloromethyltriphenylphosphonium chloride there is obtained 3-(α-chloromethylene-2,4-dichloro-β-methylphenethyl)-pyridine as an isomer-pure compound in the form of a yellow oil;

starting from 2-(2,4-dichlorophenyl)-1-(3-pyridyl)-1-propanone and methyltriphenylphosphonium bromide there is obtained 3-(2,4-dichloro-β-methyl-α-methylenephenethyl)-pyridine as a pale yellow oil;

starting from 2-(2,4-dichlorophenyl)-1-(3-pyridyl)-1-propanone and propyltriphenylphosphonium bromide there is obtained 3-(2,4-dichloro-β-methyl-α-propylidenephenethyl)-pyridine
  1st isomer: pale yellow oil,
  2nd isomer: colourless oil;

starting from 2-(2,4-dichlorophenyl)-1-(3-pyridyl)-1-butanone and methoxymethyltriphenylphosphonium chloride there is obtained 3-(2,4-dichloro-β-ethyl-α-methoxymethylenephenethyl)-pyridine as an isomer mixture in the form of a yellow oil;

starting from 2-(2,4-dichlorophenyl)-1-(3-pyridyl)-1-pentanone and methyltriphenylphosphonium bromide there is obtained 3-(2,4-dichloro-α-methylene-β-propylphenethyl)-pyridine as a pale yellow oil;

starting from 2-(2,4-dichlorophenyl)-1-(3-pyridyl)-4-pentyn-1-one and methyltriphenylphosphonium bromide there is obtained 3-(B-allyl-2,4-dichloro-α-methylenephenethyl)-pyridine as a yellow oil;

starting from 2-(2,4-dichlorophenyl)-1-(3-pyridyl)-4-pentyn-1-one and methyltriphenylphosphonium bromide there is obtained 3-[2,4-dichloro-α-methylene-β-(2-propynyl)-phenethyl]-pyridine as a yellow oil;

starting from 2-(2,4-dichlorophenyl)-1-(3-pyridyl)-4-pentyn-1-one and methoxymethyltriphenylphosphonium chloride there is obtained 3-[2,4-dichloro-α-methoxymethylene-β-(2-propynyl)-phenethyl]-pyridine
  1st isomer: white crystals, m.p. 96–97° C.,
  2nd isomer: yellowish oil;

starting from 2-(2,4-dichlorophenyl)-1-(3-pyridyl)-4-pentyn-1-one and chloromethyltriphenylphosphonium chloride there is obtained 3-[α-chloromethylene-2,4-dichloro-β-(2-propynyl)-phenethyl]-pyridine as an isomer-pure compound in the form of white crystals, m.p. 87–88° C.;

starting from 2-(2,4-dichlorophenyl)-1-(3-pyridyl)-4-pentyn-1-one and butyltriphenylphosphonium bromide 1 there is obtained 3-[α-butylidene-2,4-dichloro-β-(2-propynyl)-phenethyl]-pyridine
  1st isomer: yellow oil,
  2nd isomer: yellow oil;

starting from 2-(2,4-dichlorophenyl)-2-methyl-1-(3-pyridyl)-1-propanone and methyltriphenylphosphonium bromide there is obtained 3-(2,4-dichloro-β,β-dimethyl-α-methylenephenethyl)-pyridine as a yellow starting from 2',4'-dichloro-2-methyl-2-(3-pyridyl)-propiophenone and methyltriphenylphosphonium bromide there is obtained 3-(2,4-dichloro-α-dimethyl-β-methylenephenethyl)-pyridine as pale yellow crystals, m.p. 58–63° C.;

starting from 2,4-dichlorophenyl 1-(3-pyridyl)-cyclopropyl ketone and methyltriphenylphosphonium bromide there is obtained 3-[1-(2,4-dichloro-α-methylenebenzyl)-cyclopropyl]-pyridine as a yellowish oil;

starting from 2,4-dichlorophenyl 1-(3-pyridyl)-cyclopropyl ketone and methoxymethyltriphenylphosphonium chloride there is obtained 3-[1-(2,4-dichloro-α-methoxymethylenebenzyl)-cyclopropyl]-pyridine as an isomer mixture in the form of a yellow oil;

starting from 2,4-dichlorophenyl 1-(3-pyridyl)-cyclopropyl ketone and ethyltriphenylphosphonium bromide there is obtained 3-[1-(2,4-dichloro-α-ethylidenebenzyl)-cyclopropyl]-pyridine as an isomer mixture (about 10:1) in the form of a yellowish oil.

EXAMPLE 2

A solution of 2.5 g of 3-[1-(2,4-dichloro-α-methylenebenzyl)-cyclopropyl]-pyridine and 1.9 g of 3-chloroperbenzoic acid (85%) in 30 ml of chloroform is stirred at room temperature for 1 hour, washed with 10% potassium carbonate solution, then twice with water and dried over anhydrous sodium sulphate. The solvent is distilled off under reduced pressure, whereby 2.6 g of 3-[1-(2,4-dichloro-α-methylenebenzyl)-cyclopropyl]-pyridine 1-oxide remain behind as a colourless oil.

EXAMPLE 3

Solutions of 2 g of 3-(2,4-dichloro-B, B-dimethyl-α-methylenephenethyl)-pyridine in 80 ml of chloroform and 5 g of copper(II) acetate in 30 ml of water are shaken together vigorously. The organic phase is then dried over anhydrous sodium sulphate, filtered and evaporated to dryness. After recrystallization of the residue from diethyl ether/n-hexane there are obtained 1.2 g of the 1:1 complex of 3-(2,4-dichloro-β,β-dimethyl-α-methylenephenethyl)-pyridine and copper(II) acetate as green crystals, m.p. 190–192° C.

The mother liquor, evaporated to dryness, is dissolved in 50 ml of chloroform and again treated in the manner described above, whereby a further 0.68 g of copper complex is obtained.

In an analogous manner, starting from 3-[1-(2,4-dichloro-α-methylenebenzyl)-cyclopropyl]-pyridine there is obtained the 1:1 complex of 3-[1-(2,4-dichloro-α-methylenebenzyl)-cyclopropyl]-pyridine and copper(II) acetate as green crystals, m.p. 183° C.;

starting from 3-(α-butylidene-2,4-dichloro-β-methylphenethyl)-pyridine (1st isomer) there is obtained the 1:1 complex of 3-(α-butylidene-2,4-dichloro-β-methylphenethyl)-pyridine and copper(II) acetate as green crystals, m.p. 179–180° C. (1st isomer);

starting from 3-(2,4-dichloro-β-methyl-α-methylenephenethyl)-pyridine there is obtained the 1:1 complex of 3-(2,4-dichloro-β-methyl-α-methylenephenethyl)-pyridine and copper(II) acetate as green crystals, m.p. 202–203° C.;

starting from 3-(α-butylidene-2,4-dichloro-β-methylphenethyl)-pyridine (2nd isomer) there is obtained the 1:1 complex of 3-(α-butylidene-2,4-dichloro-β-methylphenethyl)-pyridine and copper(II) acetate as green crystals, m.p. 160–161° C. (2nd isomer);

starting from 3-(2,4-dichloro-β-methyl-α-propylidenephenethyl)-pyridine there is obtained the 1:1 complex of 3-(2,4-dichloro-β-methyl-α-propylidenephenethyl)-pyridine and copper(II) acetate as green crystals, m.p. 191–192° C.;

starting from 3-[2,4-dichloro-α-methoxymethylene-β-(2-propynyl)-phenethyl]-pyridine there is obtained the 1:1 complex of 3-[2,4-dichloro-α-methoxymethylene-β-(2-propynyl)-phenethyl]-pyridine and copper(II) acetate as green crystals, m.p. 145° C.

II. Production of the starting materials of formula II

EXAMPLE 4

8.72 g of sodium hydride (55% in oil) are added portionwise at 0° to 5° C. while stirring and under an inert gas to a solution of 26.6 g of 2',4'-dichloro-2-(3-pyridyl)-acetophenone in 120 ml of anhydrous tetrahydrofuran. After stirring at room temperature for 1.5 hours 0 the reaction mixture is allowed to cool to −75° C. and at this temperature a solution of 12.45 ml of methyl iodide in 20 ml of tetrahydrofuran is added dropwise. The mixture is left to come to room temperature during about 16 hours, poured on to ice-water and extracted three times with 100 ml of methylene chloride each time. After washing with water and distilling off the solvent under reduced pressure the residue is chromatographed on silica gel with diethyl ether as the eluent. The product is crystallized from n-hexane and there are thus obtained 15 g of 4'-dichloro-2-methyl-2-(3-pyridyl)-propiophenone as beige crystals, m.p. 75–76° C.

In an analogous manner, starting from 2,4-dichlorobenzyl (3-pyridyl) ketone there is obtained 2-(2,4-dichlorophenyl)-2-methyl-1-(3-pyridyl)-1-propanone as pale brown crystals, m.p. 103–104° C.

EXAMPLE 5

54 g of 2',4'-dichloro-2-(3-pyridyl)-acetophenone are added portionwise under an inert gas to a suspension of 46.5 g of freshly sublimed potassium tert.butylate in 590 ml of tert.butanol and the reaction mixture is stirred at 45° C. for 2 hours. The mixture is treated at room temperature with 59.5 g of 2-chloroethyl-dimethylsulphonium iodide and a spatula tip of sodium iodide and the mixture is held at 50° C. for 16 hours while stirring vigorously. The mixture is poured into water and extracted three times with 300 ml of diethyl ether each time. The combined organic extracts are washed with water, dried over anhydrous sodium sulphate and evaporated under reduced pressure. The residue is chromatographed on silica gel with diethyl ether as the eluent and crystallized from diethyl ether/n-hexane. There are obtained 41.7 g of 2,4-dichlorophenyl 1-(3-pyridyl)-cyclopropyl ketone as white crystals, m.p. 83° C.

III. Formulation Examples

EXAMPLE 6

An emulsifiable concentrate has the following composition

|  | g/liter |
|---|---|
| Active ingredient (compound in accordance with the invention) | 500 |
| Nonylphenol polyethoxylate (non-ionic emulsifier) | 50 |
| Calcium dodecylbenzenesulphonate (anionic emulsifier) | 25 |
| Mixture of $C_{10}$-alkylbenzenes (solvent) | ad 1 l |

The active ingredient and the emulsifiers are taken up in the solvent. A ready-for-use spray liquor of any desired concentration can be manufactured by emulsifying this concentrate.

EXAMPLE 7

A seed dressing composition has the following composition:

|  | Weight percent |
|---|---|
| Active ingredient (compound in accordance with the invention) | 10.9 |
| Sodium lauryl sulphate (wetting agent) | 2.0 |
| Sodium lignosulphonate (dispersing agent) | 4.0 |
| Dextrin (binding agent) | 10.0 |
| Red iron oxide (colouring agent) | 9.0 |
| Silicic acid (carrier material) | 15.0 |
| Kaolin (carrier material) | ad 100 |

The components are mixed with one another and the mixture is ground finely in a suitable mill. For application, the composition can be mixed directly in the dry state with the seeds or, by the addition of water, can be converted firstly into a flowable slurry which can then be distributed on the seeds.

EXAMPLE 8

A spray powder has the following composition:

|  | Weight percent |
|---|---|
| Active ingredient (compound in | 25.0 |

| -continued | Weight percent |
|---|---|
| accordance with the invention, especially copper complex) | |
| Sodium lauryl sulphate (wetting agent) | 4.0 |
| Sodium lignosulphonate (dispersing agent) | 10.0 |
| Silicic acid (carrier material) | 15.0 |
| Kaolin (carrier material) | ad 100 |

The components are mixed with one another and the mixture is ground finely in a suitable mill. A ready-for-use spray liquor is obtained by dispersing the mixture in water.

What is claimed is:

1. A compound of the formula

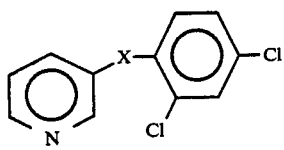   I wherein
X signifies a group (a) or (b)

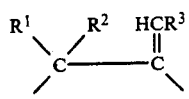   (a)

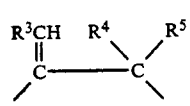   (b)

$R^1$ and $R^2$ signify methyl or together form ethylene,
$R^3$ signifies hydrogen, chlorine, $C_{1-4}$-alkyl or methoxy,
$R^4$ signifies hydrogen or methyl and
$R^5$ signifies methyl or, where $R^4$ signifies hydrogen, also $C_{1-4}$-alkyl, allyl or propargyl or
$R^4$ and $R^5$ together form ethylene,
an N-oxide, N-amino salt or a copper complex of a compound of the formula 1 or an acid addition salt of a compound of the formula 1 or their N-oxide thereof.

2. The compound according to claim 1, wherein $R^1$ and $R^2$ together form ethylene.

3. The compound according to claim 1 or 2, wherein $R^3$ signifies hydrogen or methoxy.

4. The compound according to claim 1 or 2, wherein $R^4$ signifies hydrogen.

5. The compound according to claim 1 or 2, wherein $R^5$ signifies methyl.

6. The compound according to claim 1, selected from the group consisting of:
3-(2,4-Dichloro-α,α-dimethyl-β-methylenephenethyl)-pyridine,
3-[1-(2,4-dichloro-α-methylenebenzyl)-cyclopropyl]-pyridine,
the 1:1 complex of 3-[1-(2,4-dichloro-α-methylenebenzyl)-cyclopropyl]-pyridine and copper(II) acetate,
3-[1-(2,4-dichloro-α-methylenebenzyl)-cyclopropyl]-pyridine 1-oxide,
3-[1-(2,4-dichloro-α-methoxymethylenebenzyl)-cyclopropyl]-pyridine,
3-[1-(2,4-dichloro-α-ethylidenebenzyl)-cyclopropyl]-pyridine,
3-(2,4-dichloro-α-methoxymethylene-β-methylphenethyl)-pyridine,
3-(α-butylidene-2,4-dichloro-β-methylphenethyl)-pyridine,
3-(2,4-dichloro-β,β-dimethyl-α-methylenephenethyl)-pyridine,
3-[2,4-dichloro-α-methylene-β-(2-propynyl)-phenethyl]-pyridine,
3-[2,4-dichloro-α-methoxymethylene-β-(2-propynyl)-phenethyl]-pyridine,
3-(2,4-dichloro-α-methylene-β-propylphenethyl)-pyridine,
3-(α-chloromethylene-2,4-dichloro-β-methylphenethyl)-pyridine,
3-[α-chloromethylene-2,4-dichloro-β-(2-propynyl)-phenethyl]-pyridine,
3-(β-allyl-2,4-dichloro-α-methylenephenethyl)-pyridine,
the 1:1 complex of 3-(α-butylidene-2,4-dichloro-β-methylphenethyl)-pyridine and copper (II) acetate,
3-[α-butylidene-2,4-dichloro-β-(2-propynyl)-phenethyl]-pyridine,
3-(2,4-dichloro-β-methyl-α-methylenephenethyl)-pyridine,
the 1:1 complex of 3-(2,4-dichloro-β-methyl-α-methylenephenethyl)-pyridine and copper(II) acetate and
3-(2,4-dichloro-β-ethyl-α-methoxymethylenephenethyl)-pyridine.

7. A fungicidal composition which contains an effective amount of a compound of the formula

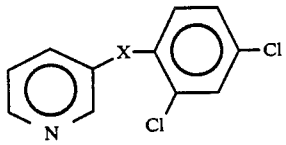   I wherein
X signifies a group (a) or (b)

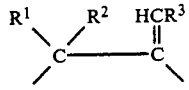   (a)

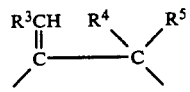   (b)

$R^1$ and $R^2$ signify methyl or together form ethylene,
$R^3$ signifies hydrogen, chlorine, $C_{1-4}$-alkyl or methoxy,
$R^4$ signifies hydrogen or methyl and
$R^5$ signifies methyl or, where $R^4$ signifies hydrogen, also $C_{1-4}$-alkyl, allyl or propargyl or
$R^4$ and $R^5$ together form ethylene,
or of a N-oxide, N-amino salt or copper complex of such a compound or of an acid addition salt of a compound of formula I or of its N-oxide as well as formulation adjuvants.

8. The fungicidal composition according to claim 7, which contains an effective amount of at least one compound selected from the group consisting of:

3-(2,4-dichloro-α,α-dimethyl-β-methylenephenethyl)-pyridine,
3-[1-(2,4-dichloro-α-methylenebenzyl)-cyclopropyl]-pyridine,
The 1:1 complex of 3-[1-(2,4-dichloro-α-methylenebenzyl)-cyclopropyl]-pyridine and copper(II) acetate,
3-[1-(2,4-dichloro-α-methylenebenzyl)-cyclopropyl]-pyridine 1-oxide,
3-[1-(2,4-dichloro-α-methoxymethylenebenzyl)-cyclopropyl]-pyridine,
3-[1-(2,4-dichloro-α-ethylidenebenzyl)-cyclopropyl]-pyridine,
3-(2,4-dichloro-α-methoxymethylene-β-methylphenethyl)-pyridine,
3-(α-butylidene-2,4-dichloro-β-methylphenethyl)-pyridine,
3-(2,4-dichloro-β,β-dimethyl-α-methylenephenethyl)-pyridine,
3-[2,4-dichloro-α-methylene-β-(2-propynyl)-phenethyl]-pyridine,
3-[2,4-dichloro-α-methoxymethylene-β-(2-propynyl)-phenethyl]-pyridine,
3-(2,4-dichloro-α-methylene-β-propylphenethyl)-pyridine,
3-(α-chloromethylene-2,4-dichloro-β-methylphenethyl)-pyridine,
3-[α-chloromethylene-2,4-dichloro-β-(2-propynyl)-phenethyl]-pyridine,
3-(β-allyl-2,4-dichloro-α-methylenephenethyl)-pyridine,
the 1:1 complex of 3-(α-butylidene-2,4-dichloro-β-methylphenethyl)-pyridine and copper(II) acetate,
3-[α-butylidene-2,4-dichloro-β-(2-propynyl)-phenethyl]-pyridine,
3-(2,4-dichloro-β-methyl-α-methylenephenethyl)-pyridine,
the 1:1 complex of 3-(2,4-dichloro-β-methyl-α-methylenephenethyl)-pyridine and copper (II) acetate and
3-(2,4-dichloro-β-ethyl-α-methoxymethylenephenethyl)-pyridine
as well as formulation adjuvants.

9. A method for the control of fungi in agriculture and n horticulture, which method comprises treating the locus to be protected with an effective amount of a compound in accordance with claim 1.

10. A method for the control of fungi in agriculture and in horticulture, which method comprises treating the locus to be protected with an effective amount of a composition in accordance with claim 7.

* * * * *